United States Patent
Kim et al.

(10) Patent No.: US 12,259,386 B2
(45) Date of Patent: Mar. 25, 2025

(54) METHOD FOR CO-DIAGNOSIS OF RALSTONIA SOLANACEARUM AND FUSARIUM OXYSPORUM BY USING SEMI-QUANTITATIVE LATERAL FLOW IMMUNODIAGNOSTIC TECHNIQUE AND KIT FOR USE THEREIN

(71) Applicants: VETALL LABORATORIES, Goyang-si (KR); ABC CIRCLE CO., LTD., Goesan-gun (KR)

(72) Inventors: Jihyun Kim, Gimpo-si (KR); Miyoung Yang, Incheon (KR); Jeongmi Kim, Goyang-si (KR); Inseo Park, Hwaseong-si (KR); Jaejun Lee, Osan-si (KR)

(73) Assignees: VETALL LABORATORIES, Goyang-si (KR); ABC CIRCLE CO., LTD., Goesan-gun (KR)

( * ) Notice: Subject to any disclaimer, the term of this patent is extended or adjusted under 35 U.S.C. 154(b) by 921 days.

(21) Appl. No.: 17/420,381

(22) PCT Filed: Dec. 17, 2019

(86) PCT No.: PCT/KR2019/017888
§ 371 (c)(1),
(2) Date: Jan. 5, 2022

(87) PCT Pub. No.: WO2020/141762
PCT Pub. Date: Jul. 9, 2020

(65) Prior Publication Data
US 2022/0128552 A1    Apr. 28, 2022

(30) Foreign Application Priority Data
Jan. 3, 2019   (KR) .................. 10-2019-0000926

(51) Int. Cl.
| | | |
|---|---|---|
| G01N 33/543 | (2006.01) | |
| C07K 16/12 | (2006.01) | |
| C07K 16/14 | (2006.01) | |
| G01N 33/569 | (2006.01) | |

(52) U.S. Cl.
CPC ... *G01N 33/54388* (2021.08); *C07K 16/1203* (2013.01); *C07K 16/14* (2013.01); *G01N 33/56911* (2013.01); *G01N 33/56961* (2013.01); *C07K 2317/14* (2013.01); *C07K 2317/33* (2013.01)

(58) Field of Classification Search
None
See application file for complete search history.

(56) References Cited

FOREIGN PATENT DOCUMENTS

| KR | 20110091719 A | 8/2011 |
| KR | 20120068674 A | 6/2012 |
| KR | 20150031229 A | 3/2015 |
| KR | 20150049136 A | 5/2015 |
| KR | 20170139199 A | 12/2017 |

OTHER PUBLICATIONS

International Search Report of PCT/KR2019/017888, Mar. 27, 2020, English translation.
Maksim Nikitin et al, Preserved Microarrays for Simultaneous Detection and Identification of Six Fungal Potato Pathogens with the Use of Real-Time PCR in Matrix Format, buisensors, Dec. 13, 2018, pp. 1-18, vol. 8, No. 129, MDPI, Basel, Switzerland.
N. Rajeshwari et al, Development of ELISA for the detection of Ralstonia solanacearum in tomato: its application in seed health testing, Would Journal of Microbiology & biotechnology, 1998, vol. 14, pp. 697-704, Springer, Berlin, Germany.
Monalisa Ray et al, Development and evaluation of polyclonal antibodies for detection of Phythium aphanidermatum and Fusarium oxysporum in ginger, Food and Agricultural Immunology, Aug. 18, 2017, vol. 29, No. 1, pp. 204-215, Taylor & Francis Group, Oxfordshire, United Kingdom.

*Primary Examiner* — Oluwatosin A Ogunbiyi
(74) *Attorney, Agent, or Firm* — STIP Law Group, LLC

(57) ABSTRACT

The present invention relates to an immunodiagnostic kit and method for co-detection of *R. solanacearum* and *F. oxysporum* that cause bacterial wilt disease and fungal wilt disease, respectively, which are difficult to accurately diagnose due to the overlapping onset time and similar disease symptoms thereof in plants, and to a test kit for determining a pathogen of plant wilt disease in an early stage by using a semi-quantitative lateral flow immunodiagnostic technique to detect the pathogen in a plant juice.

7 Claims, 6 Drawing Sheets

[FIG. 1]
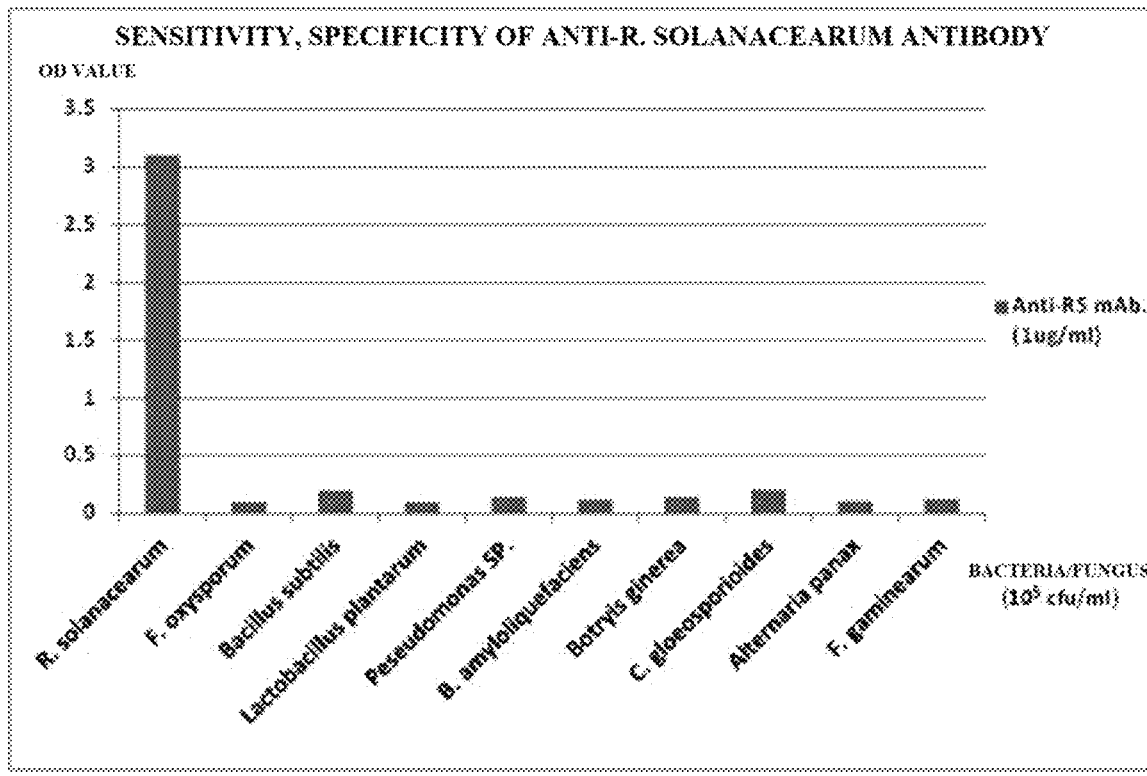
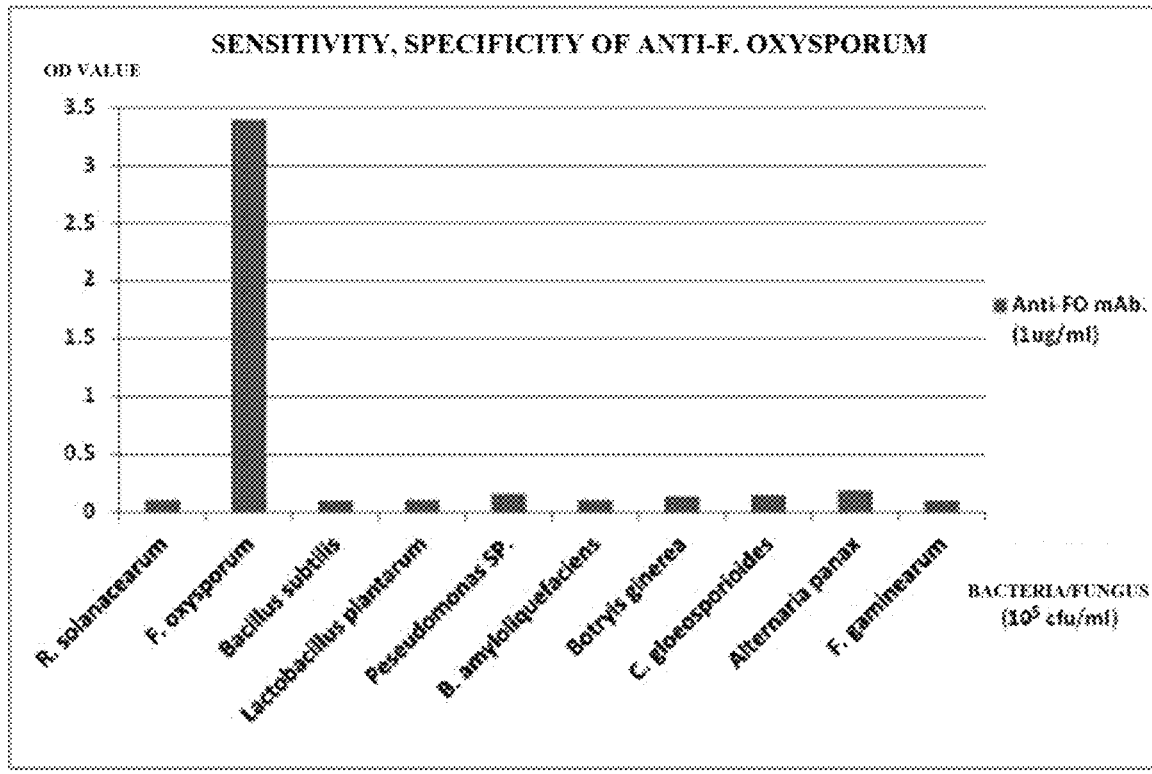

[FIG. 2]
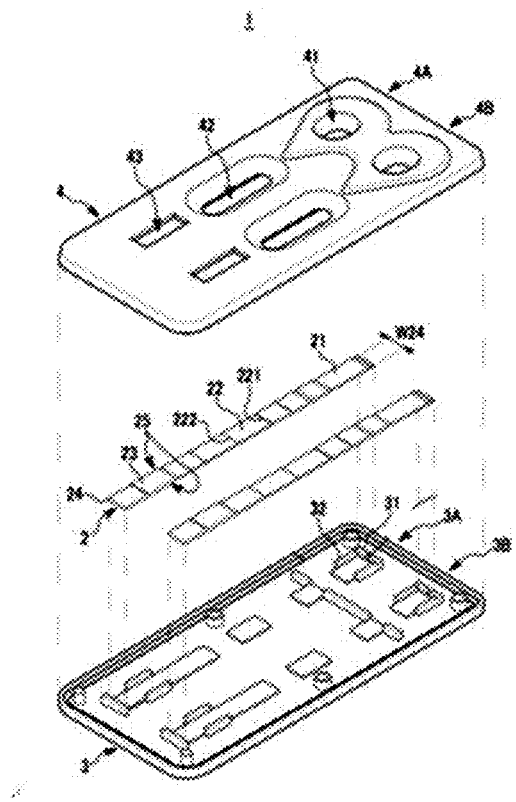
[FIG. 3A]

[FIG. 3B]
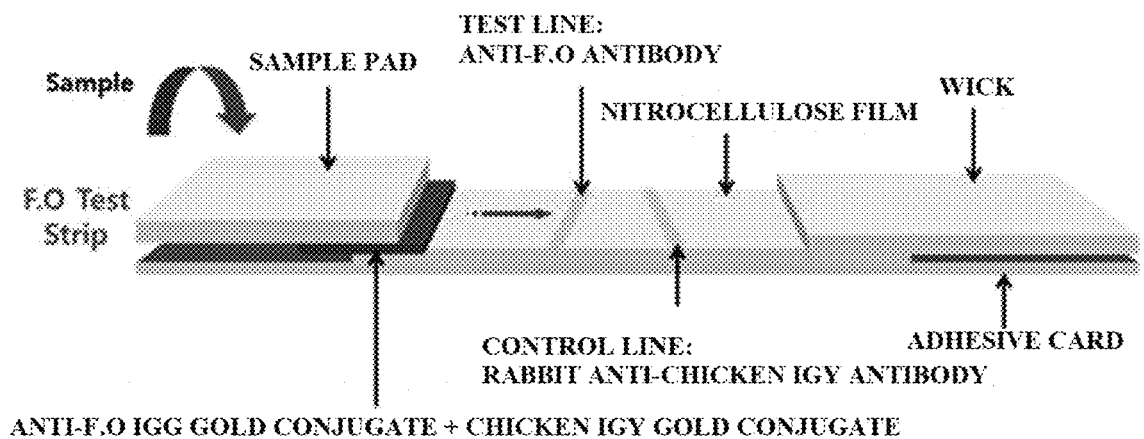
[FIG. 4]
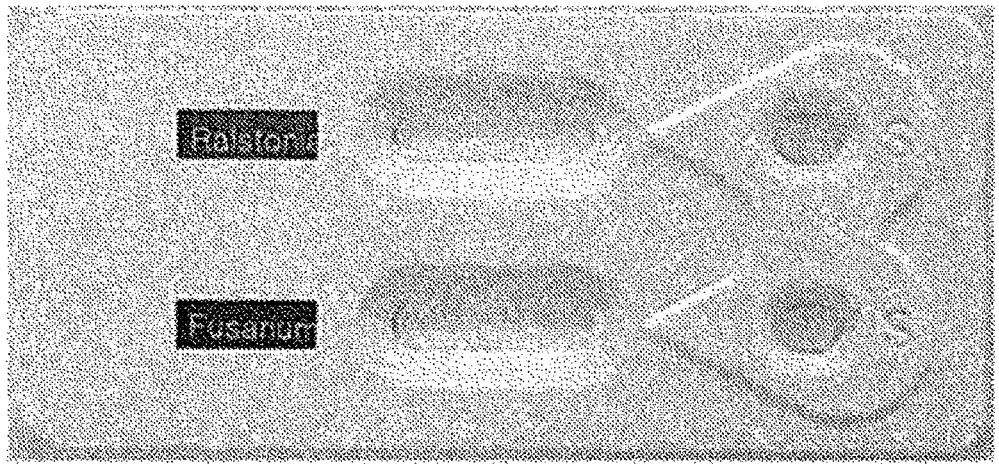

[FIG. 5]

[FIG. 6A]

| R. SOLANACEARUM STRIP | LINE INTENSITY (Control Vs Test) | DEGREE OF INJECTION |
|---|---|---|
|  | C < T. | R.S. $\geq 10^7$ cfu/ml. |
|  | C = T. | R.S. $= 10^6$ cfu/ml. |
|  | C > T. | R.S. $\leq 10^5$ cfu/ml. |
|  | Non. | R.S. Negative or. $\leq 10^4$ cfu/ml. |

[FIG. 6B]

| F. OXYSPORUM STRIP | LINE INTENSITY (Control vs Test) | DEGREE OF INJECTION |
|---|---|---|
| | C < T | F.O. ≥ $10^5$ cfu/ml |
| | C = T | F.O. = $10^3$ cfu/ml |
| | C > T | F.O. ≤ $10^3$ cfu/ml |
| | Non | F.O

METHOD FOR CO-DIAGNOSIS OF RALSTONIA SOLANACEARUM AND FUSARIUM OXYSPORUM BY USING SEMI-QUANTITATIVE LATERAL FLOW IMMUNODIAGNOSTIC TECHNIQUE AND KIT FOR USE THEREIN

CROSS-REFERENCE TO RELATED APPLICATIONS

This application is the U.S. National Phase under 35 U.S.C. § 371 of International Application No. PCT/KR2019/017888 filed on Dec. 17, 2019, which in turn claims the benefit of Korean Application No. 10-2019-0000926 filed on Jan. 3, 2019, the disclosures of which are incorporated by reference into the present application.

TECHNICAL FIELD

This disclosure relates to a method for co-diagnosis of *Ralstonia solanacearum* and *Fusarium oxysporum* by using semi-quantitative lateral flow immunodiagnostic technique and a kit for use therein. More particularly, this disclosure relates to a method for co-diagnosis of infections of *Ralstonia solanacearum* (R.S) that causes a bacterial wilt disease and *Fusarium oxysporum* (F. O) that causes a fungal wilt disease which are difficult to be diagnosed due to overlapping onset time and similar disease symptoms in plants, by using a specific antibody, and a diagnostic kit for semi-quantitatively diagnosing density of the infected pathogens.

BACKGROUND ART

A wilt disease is divided into two diseases; a bacterial wilt disease caused by *R. solanacearum* and a fungal wilt disease caused by *F. oxysporum*. These two types of wilt diseases are one of the diseases most damaging horticultural crops, but, their onset time and disease symptoms are similar so that farmers are not able to deal with them with accurate diagnosis and treatment. Farmers tend to rely on their own experiences to determine the infections, but an inaccurate diagnosis may cause a side effect of simultaneous use of chemicals for both bacterial disease and fungal disease. In addition, mixed use of various bactericides may cause aggravation of operating costs of farmers and severe environmental pollution. The pathogens of the above two diseases have a very fast disease-progressing rate, causing rapid transfer of disease to other plants, and if the pathogens are not treated properly at the early stage of infection, it is hard to control them even with chemical pesticides, possibly causing severe direct damages by causing death of crops.

Accordingly, many methods that may effectively prevent pathogen of the above two plant wilt diseases have been researched. For example, Korea Laid-open Patent Publication No. 2012-0068674 (prior art 1) discloses "*Capsicum* blight and garlic black rot fungal disease control composition comprising *Streptomyces griseus* BIG105 strain (deposit number: KCTC 11703BP) as an active ingredient" with the title of "*STREPTOMYCES GRISEUS* BIG105 FOR CONTROLLING PLANT DISEASES AND USES THEREOF", Korea Laid-open Patent Publication No. 2015-0049136 (prior art 2) discloses "a composition for controlling a plant disease comprising a strain of *Bacillus amyloliquefaciens* M27 KACC91208P M27 which cultivates the prepared strain at 26 to 33° C. for 2 to 3 days in an LB medium to prepare a culture solution or culture filtrate excluding the cells for the culture solution as an active ingredient, wherein an inhibitory effect is shown with respect to powdery mildew selected from at least one of *Podosphaera fusca* causing powdery mildew of cucumber, pumpkin, melon, watermelon, oriental melon, and gourd, *Sphaerotheca aphanis* causing powdery mildew of strawberry, *Sphaerotheca pannosa* causing powdery mildew of rose, *Erysiphe cichoracearum* causing powdery mildew of tomato, *Leveillula taurica* causing powdery mildew of pepper; an inhibitory effect is shown with respect to at least one plant pathogen fungus selected from *Alternaria* sp., *Colletotrichum panacicola*, *Cylindrocarpon destructans*, and *Pythium* sp.; an inhibitory effect is shown with respect to *Pectoacterium carotovora* sub sp. *cartovorum* causing vegetable soft rot, *Acidovorax citrulli* causing fruit rot of watermelon, *Agrobacterium tumefacienes* causing clubroot of vegetables and fruits, *Burkholderia glumae* causing bacterial grain rot, and *Ralstonia solanacearum* causing bacterial wilt disease of eggplant, and wherein the effect of promoting growth of tomato or red pepper is included, with the title of "COMPOSITION FOR CONTROLLING PLANT DISEASE AND METHOD FOR MANUFACTURING SAME."

However, the prior arts including the inventions above relate to a method for remedying the wilt diseases which have already occurred, by killing or restraining pathogens, and there have rarely been suggestions for methods or tools of diagnosing the infections of pathogens that cause a specific wilt disease and a level of infection thereof. In the meantime, Korean Laid-open Patent Publication No. 2015-0031229 (prior art 3), which is purposed to detect, identify, and quantify pathogenic and non-pathogenic organisms by using nucleic acid amplification technology discloses, "A method of quantifying a specific product in a nicking and extended amplification reaction, comprising: (a) a polymerase, two or more primer oligonucleotides (each complementary sequence on the target nucleic acid molecule) under substantially isothermal conditions, a cleavage enzyme, and a detectable polynucleotide probe, wherein each primer oligonucleotide comprises one or more 2'modified nucleotides located at the 3'end of a sequence complementary to the target nucleic acid molecule; (b) generating an amplicon comprising at least a portion of the target nucleic acid molecule; and (c) detecting an atypical signal specific for hybridization of an oligonucleotide probe to a target nucleic acid molecule or an amplicon thereof, wherein the signal is indicative of an amount of a target nucleic acid molecule or an amplicon thereof present in the sample."

However, the method disclosed in prior art 3 is designed to detect, identify and quantify pathogenic and non-pathogenic organisms by the complicated steps, and it is meaningless to diagnose those two types of wilt diseases that frequently occur in farms by using the above methods. Therefore, there has been a constant need for the diagnostic kits that could diagnose them in a simpler and desirably simultaneous manner as well as that could practicably realize them in a quantitative manner.

Accordingly, the present inventors have recognized the problems in this technical field as described above, and in order to solve the problems of the related art that diagnosis of the two types of wilt disease is not accurate and rapid analysis is not possible, the present method for enabling scientific and accurate diagnosis, and a diagnostic kit used in the method is proposed.

RELATED ART DOCUMENTS

Prior Arts (Prior art 1): Korean Laid-open Patent Publication No. 2012-0068674

(Prior art 2): Korean Laid-open Patent Publication No. 2015-0049136

(Prior art 3): Korean Laid-open Patent Publication No. 2015-0031229

DISCLOSURE

Technical Problem

The present invention considers technical problems of the prior arts described above, and the major objective of the present invention is to provide an antibody that specifically binds to R. solanacearum and F. oxysporum to detect bacterial or fungal pathogens causing wilt diseases in plants with a high specificity and sensitivity.

Another objective of the present invention is to provide a method that can measure the degrees of infections of the pathogens that can infect plants in a semi-quantitative manner by using an antibody that specifically binds to R. solanacearum and F. oxysporum.

A still another objective of the present invention is to provide a diagnostic kit that can measure the degrees of infection of the pathogens that can infect plants in a semi-quantitative manner by using an antibody that specifically binds to R. solanacearum and F. oxysporum.

The present invention may aim to achieve other objectives that can be easily derived from those skilled in the art in the field from the overall technologies of the present disclosure.

The above objectives of the present invention could be achieved to produce antibody that specially binds to R. solanacearum and F. oxysporum, and by using the above antibodies for the semi-quantitative lateral flow immunodiagnostic technique, to provide a diagnostic kit that can rapidly and easily distinguish and diagnose two pathogens, R. solanacearum and F. oxysporum, at the same time within ten minutes. More specifically, by using semi-quantitative lateral flow immunodiagnostic technique, the objectives of the present invention could be achieved by preparing a kit that can diagnose pathogens of a disease at an early stage by simultaneously diagnosing infections of pathogens causing bacterial wilt disease and fungal wilt disease and determining the degree of infections by using semi-quantitative method, and an antibody used therein.

Technical Solution

In order to address the objective, a method for co-diagnosis of Ralstonia solanacearum and Fusarium oxysporum by using semi-quantitative lateral flow immunodiagnostic technique of the present invention includes:

providing antibodies of Ralstonia solanacearum causing a bacterial wilt disease and Fusarium oxysporum causing a fungal wilt disease, respectively;

coupling Ralstonia solanacearum and Fusarium oxysporum with the respective antibodies; and quantifying amounts of the coupled Ralstonia solanacearum and Fusarium oxysporum, respectively;

According to another embodiment, the respective antibodies of the Ralstonia solanacearum and Fusarium oxysporum are obtained by, with the Ralstonia solanacearum and Fusarium oxysporum as antigens, inactivating the same at a high temperature and use the same as immunogens to immunize mouse, securing monoclonal antibody specifically responsive to Ralstonia solanacearum and Fusarium oxysporum from hybridoma by conducting cell fusion for mouse splenocyte and myeloma cell (Sp2/0 Ag-18), and finally selecting antibodies of anti-R. solanacearum and anti-F. oxysporum, among the secured antibodies.

According to a still another embodiment, the anti-R. solanacearum antibody and the anti-F. oxysporum antibody do not show cross-reactivity.

According to a still another embodiment, the secured anti-R. solanacearum antibody and the anti-F. oxysporum antibody mass-produce the antibody in the hybridoma by using a method of mouse ascites generation.

According to a still another embodiment, the quantifying amounts of the Ralstonia solanacearum and Fusarium oxysporum includes identifying that low-titer is $10^5$ cfu/ml, mid-titer is $10^6$ cfu/ml, and high-titer is $10^7$ cfu/ml as for Ralstonia solanacearum, and low-titer is $10^4$ cfu/ml, mid-titer is $10^5$ cfu/ml, and high-titer is $10^6$ cfu/ml as for F. oxysporum.

According to an embodiment, a kit for co-diagnosis of infection of Ralstonia solanacearum causing a bacterial wilt disease and Fusarium oxysporum causing a fungal wilt disease semi-quantitatively, wherein the kit protects, from various contaminants, an analysis strip in which a test line having a fixed bed for immunoglobulin G (IgG) antibody specifically responsive to Ralstonia solanacearum and Fusarium oxysporum, respectively, and a control line for identifying normal operation are provided in a predetermined area on a membrane, and a regular analysis strip, and at least one of a sample inlet for inputting a sample and a result display window for observing a response result in the test line and the control line on the analysis strip is provided.

According to another embodiment, the sample is characterized as plant juice.

According to another embodiment, the kit is characterized in that two types of diagnosis strips capable of detecting each of Ralstonia solanacearum and Fusarium oxysporum R. are provided in one test kit.

According to another embodiment, a method of semi-quantitatively diagnosing pathogen by using a co-diagnosis kit of Ralstonia solanacearum and Fusarium oxysporum includes:

inputting a fixed amount of a sample into an adjacent area of an analysis strip of a kit; combining a detecting reagent with a predetermined indicator with a material for analysis of the sample to form a complex;

developing the complex on a membrane; and observing a change in appearance in a reaction unit having a fixed bed for each pathogen in the predetermined area of the membrane.

According to a still another embodiment, the method may further include in response to antibodies specific to each pathogen being coupled to the reaction unit, identifying amounts of pathogens in a sample into high-titer, mid-titer, low-titer, and negative based on comparison of a color according to reaction with a control line.

Effect of the Invention

The present invention provides a method for co-diagnosis of Ralstonia solanacearum and Fusarium oxysporum by using semi-quantitative lateral flow immunodiagnostic technique and a kit for use therein, wherein antibodies with a high sensitivity and specificity for R. solanacearum and F. oxysporum are prepared and provided, and a detection kits to which the antibody is applied is provided so as to easily detect pathogens of wilt diseases in plants using the same.

More particularly, the kit for the wilt disease in plants can semi-quantitatively analyze the sources of infections within ten minutes. Thus, as compared to previous microorganism separation and identification method and PCR analysis, and inaccurate diagnoses by naked eyes of the prior art, the kit for wilt disease in plants enables diagnosis of types and infections of pathogens that can cause diseases in plants easily and economically, and also enables the semi-quantitative analysis to easily measure and determine the degree of infections, thus enabling farmers to choose appropriate types and amount of chemicals for treatment.

DESCRIPTION OF DRAWINGS

FIG. 1 is a graph of the result of the ELISA test showing sensitivity between anti-*R. solanacearum* and anti-*F. oxysporum* as well as cross-reactivity among similar pathogens according to the present invention;

FIG. 2 is a schematic exploded perspective view of the detection kits for *R. solanacearum* and *F. oxysporum* according to the present invention;

FIG. 3A and FIG. 3B are a schematic view of the structure of the strip forming the detection kits for *R. solanacearum* and *F. oxysporum* according to the present invention;

FIG. 4 is a representative drawing of the detection kits for *R. solanacearum* and *F. oxysporum* according to the present invention;

FIG. 5 is a picture of the result from the detection kits for the exemplary titer-specific sample of *R. solanacearum* and *F. oxysporum* according to the present invention; and FIG. 6A and FIG. 6B are a graph showing interpretation of the result of the detection kits for *R. solanacearum* and *F. oxysporum* according to the present invention.

BEST MODE FOR CARRYING OUT THE INVENTION

Hereinafter, a preferred embodiment of the present invention will be described in detail with reference to the accompanying drawings. However, the scope of the present invention is not limited thereto.

These embodiments are provided so that this disclosure will be thorough and complete and will fully convey the concept of the invention to those skilled in the art, and the present disclosure will only be defined by the appended claims. Well-known components, movement and techniques among the best mode for carrying out the invention will not be described in detail to prevent ambiguous interpretation.

The terminology used in the specification is intended to describe exemplary embodiments of the present invention, without departing from the spirit or scope of the present invention. In addition, the components and operations referred to as "comprises (or includes)" do not preclude the presence or addition of one or more other components and operations.

The term "*R. solanacearum*" pathogen used herein is a Gram-negative, rod-shaped and aerobic bacteria with several flagella generating movement, may survive for several years while being incubated in soil at 34° C. and hibernate inside the remains of sick plants. It mainly invades through wounds in the underground tissue of plants, but occasionally invades through wounds in the above-ground tissue of plants. It is known that it occurs rapidly under conditions of high temperature and high humidity.

The term "*F. oxysporum*" used herein is a pathogen causing severe diseases in a variety of plants globally and comprises more than 120 species according to the host specificity that causes diseases due to high host specificity. In addition, the pathogens could remain dormant for several years by formulating chlamydospore in soil without host plants, and when the environment improves, chlamydospores germinate and invade the roots of host plants, causing wilt disease or *Fusarium* wilt disease.

According to a preferred embodiment of the present invention, the co-diagnosis for the *Ralstonia solanacearum* and *Fusarium oxysporum* using semi-quantitative lateral flow immunodiagnostic technique includes the steps of: (1) providing antibodies to *Ralstonia solanacearum* (*R. solanacearum*; R. S) that causes a bacterial wilt disease and *Fusarium oxysporum* (*F. oxysporum*; F.O) that cause a fungal wilt disease; (2) combining *R. solanacearum* and *F. oxysporum* with each antibody; (3) quantifying the each amount of *R. solanacearum* and *F. oxysporum*.

According to another preferred embodiment of the present invention, the co-diagnosis for the *Ralstonia solanacearum* and *Fusarium oxysporum* using semi-quantitative lateral flow immunodiagnostic technique includes the steps of quantifying the amount of *Ralstonia solanacearum* and *Fusarium oxysporum* comprise: (1) low-titer ($10^5$ cfu/ml), mid-titer ($10^6$ cfu/ml) and high-titer ($10^7$ cfu/ml) of *R. solanacearum*; (2) low-titer ($10^4$ cfu/ml), mid-titer ($10^5$ cfu/ml) and high-titer ($10^6$ cfu/ml) of *F. oxysporum*; (3) negative ($10^3$ cfu/ml) of *F. oxysporum*.

According to a still another preferred embodiment of the present invention, specific antibodies to *R. solanacearum* or *F. oxysporum* capable of detecting each specific pathogen can be selected without limits, but monoclonal antibodies that don't show cross-reactivity with bacteria and fungi that can infect plants are advised to be selected.

In addition, by using monoclonal antibodies specifically responsive to *solanacearum* and *F. oxysporum*, the present invention provides the semi-quantitative kits that determine causative organism by detecting increased pathogens in plants with a wilt disease and analyzing the degrees of infections.

To achieve the above objectives of the present invention, the present invention uses *R. solanacearum*, a pathogenic bacterium, and *F. oxysporum*, a pathogenic fungus as immunogens for preparing antibodies. The bacteria and fungi used in the present invention was introduced and incubated by the Korean Agricultural Culture Collection (KACC) through ABC Circle, and the incubated bacteria and fungi were inactivated at high temperature and used as immunogens to produce antibodies.

To achieve the above objectives of the present invention, this invention used inactivated bacteria and inactivated fungi as immunogens to immunize mice, and conducted cell fusion for Splenocyte cells and Myeloma cells (Sp2/0 Ag-18) to produce Hybridoma. Then, each monoclonal antibody specifically responsive to *R. solanacearum* and *F. oxysporum* were secured from the hybridoma. The sensitivity to the immunogen of the finally selected mouse's anti-*R. solanacearum* and anti-*F. oxysporum*, among the secured antibodies, is provided as the ELISA result, and the reactivity with 10 kinds of bacteria and fungi that may be present due to inflection of plants subject to the diagnosis kit, that may be present in soil, or may cause cross reactivity is provided as the ELISA result.

To achieve the objectives of the present invention, finally-selected two antibodies, mouse anti-*R. solanacearum* and anti-*F. oxysporum*, showed high sensitivity, but didn't show cross-reactivity with respect to *R. solanacearum* and *F. oxysporum*. In addition, with reference to FIG. 1, two antibodies didn't show cross-reactivity to four types of bacteria (*Bacillus subtilis, Lactobacillus plantarum, Peseudomonas* SP., *Bacillus Amyloliquefaciens*) and four types of molds (*Botrysis cinerea, Colletotrichum gloeosporioides, Alternaria panax, Fusarium graminearum*).

The two antibodies produced according to the present invention respond to *R. solanacearum* and *F. oxysporum* specifically, and this invention uses the antibodies to produce the diagnostic kits according to the present invention.

To achieve the above objectives of the present invention, by using monoclonal antibody specifically responsive to *R. solanacearum* and *F. oxysporum*, this invention captures pathogens from juice of the plants and provides an analysis strip to detect each *R. solanacearum* and *F. oxysporum* specifically by using a rapid immunochromatography.

To achieve the above objectives of the present invention, the present invention includes the steps of inputting a fixed amount of a sample into an adjacent area of an analysis strip, combining a detecting reagent with the material for analysis of the sample to form a complex, developing the complex on a membrane, observing a change in appearance in the reaction unit having a fixed bed for each pathogen in a predetermined area of the membrane.

The above diagnostic method of the present invention includes sandwich assay or competition assay.

The present invention provides a kit, which is a kit for implementing the diagnosis method above. Referring to FIG. 2, provided is a diagnosis kit for detecting *Ralstonia solanacearum* and *Fusarium oxysporum*, wherein the kit protects, from various contaminants, an analysis strip 2 in which a test line 221 having a fixed bed for immunoglobulin G (IgG) antibody specifically responsive to *Ralstonia solanacearum* and *Fusarium oxysporum*, respectively, and a control line 222 for identifying normal operation are provided in a predetermined area on a membrane 22, and a regular analysis strip, wherein at least one of a sample inlet 41 for inputting a sample and a result display window 42 for observing a response result in the test line 221 and the control line 222 on the analysis strip 2.

The above sample preferentially uses plant juice.

In order to detect *R. solanacearum* and *F. oxysporum*, which are pathogens of plant wilt disease, from plants by using the immunochromatography, the specific antibody capable of detecting pathogens in the nitrocellulose membrane is adsorbed to a predetermined position and an antibody capable of selectively binding to the pathogen is bonded to the gold particles to be dried on the pad. The dried gold conjugate pad and the pad applying the sample overlap each other to cover the nitrocellulose membrane and include a hygroscopic pad at the opposite position (Referring to FIG. 3).

Membrane that can be used for producing analysis strips according to the present invention is capable of using materials generally used for diagnostic strips, and the examples include nitrocellulose, cellulose, cellulose acetate, polyethylene, and a material that is selected from various kinds of synthetic polymer.

As for the labeled reagents that can be included in the control reagents, the same can be applied as in the detection reagents above. Auxiliary specific binding materials are not specifically limited, but can be selected from, for example, avidin, biotin, FITC, anti-FITC antibody, mouse Immunoglobulin G (IgG) or anti-mouse Immunoglobulin G antibody.

The detection reagent includes a labeled reagent, an auxiliary singular coupling member, or a signal generating system that allows the presence of an analyte to be inspected from the outside through a naked eye or other mechanism.

Labeled detection reagents are well known in the art to which the present invention belongs. The examples of labeled reagents include catalyst, enzyme (phosphatase, peroxidase), enzyme substrate (nitroblue tetrazolium 3,5', 5,5'-Tetranitrobenzidine, 6-methoxy-1-naphthol, 4-Chloro-1-naphthol, 5-Bromo-4-chloro-3-indolyl phosphate), chemiluminescence enzyme substrate (dioxetane), fluorescence compounds (fluorescein, phycobiliprotein, rhodamine), Chemiluminescence compounds, metal sol, nonmetal sol, carbon sol, dye sol, particle latex, color indicator, color materials included in liposome, or the like.

The analysis strip of the present invention is produced by putting the analysis strip in a plastic single device (immunodiagnostic analyzer) with a result display 42 in a sample inlet 41 (referring to FIG. 2). After grinding the soil surface of plants in the sample inlet 41 with sample diluted solution, three drops of the juice are put on the area of the sample dropping with the usage of a disposable dropping pipet. *R. solanacearum* and *F. oxysporum* in the sample respond to specific antibodies attached to gold particles and capillary action is displayed onto the nitrocellulose membrane 22. Specifically, the specific antibody capable of detecting each of the *solanacearum* or *F. oxysporum* is adsorbed at a predetermined position on the test line 221 of the membrane. The pathogen present in the sample is combined with the antibody conjugated to the gold particles to form a composite, and the composite forms a violet (red) band by gold particle color at the corresponding position by combining with an antibody specific to the *solanacearum* or *F. oxysporum* located in the test line while passing through the test line. In the control line 222, rabbit anti-chicken IgY is adsorbed to constantly react with the presence of pathogens in the sample regardless of whether pathogen is present in the sample, thereby showing a violet (red) band.

The non-responsive contents are absorbed in wicks, and it is easy to identify the formulated bands since membrane looks pure white. In addition, when *R. solanacearum* and *F. oxysporum* don't exist in the sample, purple or red bands are formulated in the control lines of the strip (referring to FIG. 5).

With respect to a method of diagnosing the status and degrees of infections of *R. solanacearum* and *F. oxysporum* in the plants, the interpretation of each result will be described with reference to FIG. 6 in detail.

Hereinafter, a raw material, an analysis strip, and a manufacturing method thereof according to an embodiment of the present invention will be described in detail with reference to the following examples. Although these embodiments are presented in order to understand the contents of the present invention, the scope of the present invention should not be construed as limited to the embodiment.

Exemplary Embodiment 1. Production of Antibodies to Mouse Anti-*R. solanacearum* and Anti-*F. oxysporum*

A. Preparation of Immunogens, *R. solanacearum* and *F. oxysporum*

The bacteria and fungi used as immunogens in mice were introduced and incubated in Korean Agricultural Culture Collection (KACC) through ABC Circle, and the incubated bacteria and fungi were inactivated at high temperature and used as immunogens to produce antibodies.

B. Production of Hybridoma

Two hybridomas were produced to create antibodies specifically responsive to pathogens of wilt diseases. An emulsion mixed at a ratio of 1:1 with complete adjuvant or incomplete adjuvant (Sigma), which is an immunity enhancer, was injected into a belly of a mouse (Balb/cA mouse, 8 week, and female). For two months, six times of immunity were carried out, and mice with high antibody production rate were selected and spleen was extracted. Only red blood cells were selectively removed using RBC hemolytic buffer (Sigma) in splenocytes obtained by crushing the spleen. The spleen cells which were washed three times were mixed with myeloma cells (Sp2/0: Ag-18) at a ratio of 5:1, and a cell fusion was induced by mixing PEG1500 (polyethylene glycol 1500, Sigma) by 1 ml. Hybridoma produced by fusing two kinds of cells was dispensed in the 96 well culture plate, and incubated for 1 week in the selective medium with DMEM (Hyclone) including 10% FBS (Fetal bovine serum, Hyclone) and 1×HAT media supplement (Sigma), and unfused cells were removed. After being incubated for 1 week in the culture media with DMEM (Hyclone) including 10% FBS (Fetal bovine serum, Hyclone) and 1×HAT media supplement (Sigma), cell culture media was collected, and clones that could generate specific antibodies to antigens were selected via the 1st screening. The selected clones went through the isolation process and 2nd screening to secure final monoclonal hybridoma.

C. Selection of Specific Antibody

When it comes to the selection of antibodies to anti-*R. solanacearum* and anti-*F. oxysporum*, the antibodies that shows high sensitivity to antibodies were selected, and the antibodies that do not show response to the cross-reacting materials were selected. The sensitivity and specificity of antibodies were identified via the ELISA test.

When selecting antibodies that meet the above conditions, five types of bacteria (*Ralstonia solanacearum, Bacillus subtilis, Lactobacillus plantarum, Peseudomonas S.P, Bacillus amyloliquefaciens*), five types of fungi (*Fusarium oxysporum, Botrysis cinerea, Colletotrichum gloeosporioides, Alternaria ponax, Fusarium graminearum*) were identified to determine reactivity through the ELISA test. The above 5 types of bacteria and 5 types of fungi were introduced and incubated through ABC Circle.

According to the result of the test, the anti-*R. solanacearum* antibody is selected as a final antibody which exhibits high sensitivity to *R. solanacearum*, and does not exhibit cross reactivity with respect to nine bacteria and fungi (refer to FIG. 1).

In addition, antibodies to anti-*F. oxysporum* are selected as a final antibody which showed high sensitivity to *F. oxysporum*, and does not show cross-reactivity to 9 types of bacteria and fungi (refer to FIG. 1).

D. Bulk Security of Antibody

In order to mass-produce an antibody in a secured hybridoma, a method of mouse ascites generation is used. The hybridoma was cultured and 5×10-6 cells per mouse (Balb/cA mouse, 8 week old, female) were injected into the abdominal cavity, and a plurality of ascites generated in mouse abdominal cavity was recovered after 2-3 weeks. The antibody purification was carried out using a protein G resin (HiTrap protection G HP column, GE). The purified monoclonal antibody was obtained, and a sandwich pair test was carried out to specifically react to each of *R. solanacearum* and *F. oxysporum*, and an antibody that does not show cross reactivity with other bacteria and fungi was finally selected. Finally, an antibody showing high sensitivity and specificity to *R. solanacearum*, and an antibody showing high sensitivity and specificity to *F. oxysporum* were obtained and used in the preparation of a kit according to the present invention.

Exemplary Embodiment 2. Production of Detection Strips and Diagnostic Kits for *R. solanacearum* and *F. oxysporum*

A. Preparation of membrane coated with antibodies to *R. solanacearum* and *F. oxysporum*

Two specific antibodies to each pathogen (Vetall Lab.) of which the final concentration was the 1 mg/ml concentration is used for test line, the control line is rabbit anti-chicken IgY (Rabbit anti-Chicken IgY) with the 1 mg/ml concentration. The solution of the antibody and control line of the test line was coated in a nitrocellulose membrane using a dispensing mechanism (KINAMETICS, USA). It was dried overnight in a laboratory of low humidity or dried in a pan for at least 5 hours. The plate of the manufactured membrane was kept in a sealed container or in a laboratory with low humidity with a drying agent.

B. Production of Antibody Gold Conjugates

Mouse Anti-*R. solanacearum* antibody (Vetall Lab.) was agitated so that the final concentration reaches 18 ug/ml and was added dropwise to the gold solution. In addition, the mouse anti-*F. oxysporum* antibody (Vetall Lab) was agitated so that the final concentration reaches 16 ug/ml and added dropwise to the gold solution. Each two solution was again agitated for 15 minutes. Then, a 10% BSA solution was added to each gold particle suspension. After agitating the solution again for 15 minutes, combined gold solution was isolated through the process of centrifugation, and the supernatant was deserted to eliminate uncombined antibodies. By adding 5 mM Sodium Tetraborate (pH 7.2) with 1% BSA which is three times of the capacity of pellet to combined gold solution (pellet), and then the above pellet was again suspended. After suspensions were again isolated through the process of centrifugation, final pellet with 5 mM Sodium Tetraborate (pH 7.2) added with 1% of BSA was produced by adjusting the absorbance to 10±1 O.D. in the spectrophotometer (530 nm).

C. Production of Chicken IgY Antibody Combined with Gold Conjugates

While agitating the chicken IgY (Fitzgerald, 70-B9093RA00-A0) so that the final concentration reaches 20 ug/ml, and was added dropwise to the gold solution, and the solution were again agitated for 15 minutes. After that, 10% BSA solution was added to the suspensions of gold particles. After agitating the solution again for 15 minutes, combined gold solution was isolated through the process of centrifugation, and the supernatant was deserted to eliminate uncombined antibodies. By adding 5 mM Sodium Tetraborate (pH 7.2) with 1% BSA with 3× capacity of pellet to combined gold solution (pellet), the above pellet was again suspended. After the suspensions were again isolated through the process of centrifugation, final pellet with 5 mM Sodium Tetraborate (pH 7.2) added with 1% of BSA was produced by adjusting the absorbance to 10±1 O.D. in the spectrophotometer (530 nm).

D. Preparation of Pads for Gold Conjugate

The above gold conjugate which was produced in B and C was manufactured by adding 5% Trehalose.

For diagnosis strips for *R. solanacearum*, the 0.5×20 cm glass fiber was prepared such that a mouse anti-R *solanacearum* antibody-gold conjugate has a final concentration of 3.0 optical density (O.D) and the chicken IgY-gold conjugate at a final concentration of 0.5 O.D.

For diagnosis strips for *F. oxysporum*, the 0.5×20 cm glass fiber was prepared such that a mouse anti-*F. oxysporum* antibody-gold conjugate has a final concentration of 2.0 optical density (O.D) and the chicken IgY-gold conjugate at a final concentration of 0.5 O.D.

E. Production of Wicks and Sample Pads

The wicks and sample pads were produced after dehydration to absorb reacting solution.

F. Assembling of the Device

Each of the membranes and the pads prepared above was cut into a strip size suitable for the size of the immunoassay device by overlapping each of the membranes and the pads, respectively, with a sample pad, a gold pad (gold conjugate treatment pad), a nitrocellulose membrane, and finally a moisture absorption pad. The cut strip was finally placed on the lower plate of the immunoassay device for diagnosis, and a kit for co-diagnosis was prepared.

G. Product Configuration

As described above, the immunoassay device and the sample diluent, the sample dilution liquid bottle, the homogenizer, and the dropper are configured as a final product.

Exemplary Embodiment 3. Selection of Cut-Off Level of Pathogen According to the Present Invention A. To select the cut-off levels of pathogens for co-diagnosis kits for the *R. solanacearum* and *F. oxysporum* produced in the above exemplary embodiment 3, the expression concentration life test in the plant of *R. solanacearum* and *F. oxysporum* causing wilt disease was carried out by the ABC Circle. The three types of seeding in host plants (tomato, cucumber, chili) were sown for cultivation. Cultivated *R. solanacearum* and *F. oxysporum* were injected into each plant. By identifying symptoms of wilt diseases that appear in plants at 25° C. or higher, and movement and density of microorganism inside the sap were measured in the interval of five days.

As a result, when the early symptoms of the wilt disease in the *R. solanacearum* plant were confirmed with the naked eye, the pathogen density of $1\times10^5$ cfu/ml or higher was confirmed, and at least $1\times10^6$ cfu/ml or more, the wilt disease was rapidly progressed to kill plants. Density measurements were not accurately performed with microorganism separation and identification method in $1\times10^4$ cfu/m of *R. solanacearum*. When the early symptoms of the wilt disease in the *F. oxysporum* plant were confirmed with the naked eye, the pathogen density of $1\times10^4$ cfu/ml or higher was confirmed, and at least $1\times10^5$ cfu/ml or more, the wilt disease was rapidly progressed to kill plants. Density measurements were not accurately performed with microorganism separation and identification method in $1\times10^3$ cfu/m of *F. oxysporum*.

B. Based on the symptoms of wilt diseases and pathogen density, the cut-off level of pathogens in the *R. solanacearum* and *F. oxysporum* diagnosis kit was selected, and for semi-quantitative analysis, the level was determined into three tiers (low, mid, and high) as in <Table 1>.

Exemplary Embodiment 4. Effect Test of Diagnostic Strips for *R. solanacearum*

A. By using the diagnostic kits for *R. solanacearum* produced according to the above exemplary embodiment 2, the plant samples of domestic farmers were provided from ABC Circle for diagnosis. The inflection was identified by using 30 positive samples where bacterial wilt disease occurs and 20 negative samples. By using the microorganism separation and identification method, the pathogen density was measured to detect the signs of infections as in <Table 2>.

With the diagnostic kits of the present invention and Agdia Rs Immuno Strip Test, examination was conducted, and the relative sensitivity and relative specificity of the diagnostic kits were identified by measuring the number of detected samples as below <Table 3A>. The relative sensitivity shows the ratio of positive samples in the Agdia Rs Immuno Strip Test that was found positive in the diagnostic kits of the present invention, and the relative specificity shows the ratio of negative samples in the Agdia Rs Immuno Strip Test that was found negative in the diagnostic kits of the present invention.

As a result, all of the 50 samples showed the same result compared to the Agdia Rs Immuno Strip Test, and the relative sensitivity and relative specificity were 100%.

B. The examination was conducted based on the diagnostic kits of the present invention and the microorganism separation and identification method, and the titer-specific relative sensitivity and relative specificity of the diagnostic kits were identified by measuring the number of detected samples as below <Table 3B>.

The titer-specific relative sensitivity shows the ratio in the density of pathogen from microorganism separation and identification method that also showed the same titer in the diagnostic kits for *R. solanacearum* according to the present invention.

As a result, the titer-specific relative sensitivity was 100% (high titer), 90% (medium titer) and 92% (low titer).

Therefore, the performance of the diagnostic kits according to the present invention was outstanding.

Exemplary Embodiment 5. Effect Test of Diagnostic Strips for *F. oxysporum*

A. By using the diagnostic kits for *F. oxysporum* produced according to the above exemplary embodiment 2, the plant samples of domestic farmers were provided from ABC Circle for diagnosis. Here, 19 positive samples where fungal wilt disease occurred and 31 negative samples were used to detect the signs of infections. By using the microorganism separation and identification method, the pathogen density was measured to detect the signs of infections as in <Table 2>.

With the diagnostic kits of the present invention and the microorganism separation and identification method, the examination was conducted, and the relative sensitivity and relative specificity of the diagnostic kits were identified by measuring the number of detected samples as below <Table 4>.

The titer-specific relative sensitivity shows the ratio in the density of pathogen from the microorganism separation and identification method that also showed the same titer in the diagnostic kits for *F. oxysporum* according to the present invention.

As a result, the titer-specific relative sensitivity was 100% (high-titer), 90% (mid-titer) and 100% (low-titer). Therefore, the performance of the diagnostic kits according to the present invention was outstanding.

TABLE 1

Selection of cut-of level of diagnostic kits for *R. Solanacearum* and *F. Oxys

TABLE 2-continued

Comparison of Performance of Diagnostic Kits for R. Solanacearum and F. Oxysporum

| No. | Sample | Microorganism separation and identification method for R.S (cfu/ml) | Agida Rs ImmunoStrip | The kit of the present invention | Microorganism separation and identification method for F.O (cfu/ml) | The kit of the present invention |
|---|---|---|---|---|---|---|
| 48 | Cucumber | $3.8 \times 10^6$ | Positive | Mid-Titer | $\leq 10^3$ | Negative |
| 49 | Tomato | $4.4 \times 10^6$ | Positive | Mid-Titer | $\leq 10^3$ | Negative |
| 50 | Tomato | $5.8 \times 10^6$ | Positive | Mid-Titer | $\leq 10^3$ | Negative |

* When the microorganism density of R. Solanacearum was at $10^4$ cfu/m or below, the measurement was not accurately conducted.
* When the microorganism density of F. Oxysporum was at $10^3$ cfu/m or below, the measurement was not accurately conducted.

TABLE 3

Relative Sensitivity and Relative Specificity of Diagnostic Kits for R. Solanacearum and Those of Other Companies

| | Agida Rs ImmunoStrip Test | | |
|---|---|---|---|
| Kits of the present invention | Positive | Negative | Total |
| 40 Samples Positive | 30 | 0 | 30 |
| Negative | 0 | 20 | 20 |
| Total | 30 | 20 | 50 |
| Relative sensitivity | | 100% | |
| Relative specificity | | 100% | |

TABLE 4

Relative Sensitivity and Relative Specificity of Diagnostic Kits for R. Solanacearum and Microorganism separation and identification method

| | | Microorganism separation and identification method (R. Solanacearum) | | | | |
|---|---|---|---|---|---|---|
| Kits of the present invention | | $\geq 10^7$ cfu/ml | $=10^6$ cfu/ml | $\leq 10^5$ cfu/ml | Negative $\leq 10^4$ cfu/ml | Total |
| 50 Samples | High-Titer $\geq 10^7$ cfu/ml | 5 | 1 | 0 | 0 | 6 |
| | Mid-Titer $=10^6$ cfu/ml | 0 | 9 | 1 | 0 | 10 |
| | Low-Titer $\leq 10^5$ cfu/ml | 0 | 0 | 12 | 2 | 14 |
| | Negative | 0 | 0 | 0 | 20 | 20 |
| Total | | 5 | 10 | 13 | 22 | 50 |
| High-Titer Relative Sensitivity | | | | 100% | | |
| Mid-Titer Relative Sensitivity | | | | 90% | | |
| Low-Titer Relative Sensitivity | | | | 92% | | |
| Relative Specificity | | | | 90% | | |

TABLE 5

Relative Sensitivity and Relative Specificity of Diagnostic Kits for F. Oxysporum and Microorganism separation and identification method

| | | Microorganism separation and identification method (F. Oxysporum) | | | | |
|---|---|---|---|---|---|---|
| Kits of the present invention | | $\geq 10^6$ cfu/ml | $=10^5$ cfu/ml | $\leq 10^4$ cfu/ml | Negative $\leq 10^3$ cfu/ml | Total |
| 50 Samples | High-Titer $\geq 10^6$ cfu/ml | 4 | 0 | 0 | 0 | 4 |
| | Mid-Titer $=10^5$ cfu/ml | 0 | 9 | 0 | 0 | 9 |
| | Low-Titer $\leq 10^4$ cfu/ml | 0 | 1 | 5 | 2 | 8 |
| | Negative | 0 | 0 | 0 | 29 | 29 |
| Total | | 4 | 10 | 5 | 31 | 50 |
| High-Titer Relative Sensitivity | | | | 100% | | |
| Mid-Titer Relative Sensitivity | | | | 90% | | |
| Low-Titer Relative Sensitivity | | | | 100% | | |
| Relative Specificity | | | | 93% | | |

As described above, it should be noted that the method for co-diagnosis of *Ralstonia solanacearum* and *Fusarium oxysporum* by using semi-quantitative lateral flow immuno-diagnostic technique and kit for use therein according to the present invention has been specifically described in the preferred embodiment, but the above-described embodiments are for purposes of illustration and are not intended to limit the scope thereof. It will be apparent to those skilled in the art that various modifications and variations are possible within the spirit and scope of the present invention, and thus these modifications and variations will be apparent to those skilled in the art.

REFERENCE NUMERALS

1 IMMUNOASSAY DEVICE
2 ANALYSIS STRIP
3 LOWER CASE
3A, 3B FIRST STRIP SUPPORT UNIT, SECOND STRIP SUPPORT UNIT

4 UPPER CASE
4A, 4B FIRST STRIP RESPONSE UNIT, SECOND STRIP RESPONSE UNIT
21 SAMPLE PAD
221 TEST LINE
222 CONTROL LINE
22 MEMBRANE
23 WICK
24 SHORT SIDE
25 LONG SIDE
31 SHORT-SIDE FIXING UNIT
32 LONG-SIDE FIXING UNIT
33 LOWER PORTION BLOCKING UNIT
41 SAMPLE INLET
42 CHARACTER DISPLAY
42 RESULT DISPLAY WINDOW

What is claimed is:

1. A method for co-diagnosis of *Ralstonia solanacearum* and *Fusarium oxysporum* by using a semi-quantitative lateral flow immunodiagnostic technique, the method comprising:
providing antibodies of *Ralstonia solanacearum* causing a bacterial wilt disease and *Fusarium oxysporum* causing a fungal wilt disease, respectively;
coupling *Ralstonia solanacearum* and *Fusarium oxysporum* in a sample with the respective antibodies by letting the sample flow laterally along a membrane such that *Ralstonia solanacearum* and *Fusarium oxysporum* meet the antibodies at a test line and a control line on the membrane; and
quantifying amounts of the coupled *Ralstonia solanacearum* and *Fusarium oxysporum*, respectively, by semi-quantitatively identifying the amount of *Ralstonia solanacearum* and *Fusarium oxysporum* in the sample into high-titer, mid-titer, low-titer or negative based on a color comparison between the test line and the control line.

2. The method of claim 1, wherein the respective antibodies of the *Ralstonia solanacearum* or *Fusarium oxysporum* are provide by, with the *Ralstonia solanacearum* or *Fusarium oxysporum* as antigens, inactivating the same at a high temperature, using the same as immunogens to immunize mouse, securing monoclonal antibody specifically responsive to *Ralstonia solanacearum* or *Fusarium oxysporum* from hybridoma by conducting cell fusion offer mouse splenocyte from the mice immunized with the *Ralstonia solanacearum* antigens or immunized with the *Fusarium oxysporum* antigens and myeloma cells (Sp2/0 Ag-18), and finally selecting antibodies of anti-*R. solanacearum* or anti-*F. oxysporum*, among the secured antibodies.

3. The method of claim 1, wherein the anti-*R. solanacearum* antibodies and the anti-*F. oxysporum* antibodies do not show cross-reactivity.

4. The method of claim 2, wherein the secured anti-*R. solanacearum* antibodies and the anti-*F. oxysporum* antibodies are mass-produced from the antibody in the hybridoma by using a method of mouse ascites generation.

5. The method of claim 1, wherein the quantifying amounts of the *Ralstonia solanacearum* and *Fusarium oxysporum* comprises identifying that low-titer is $10^5$ cfu/ml, mid-titer is $10^6$ cfu/ml, and high-titer is $10^7$ cfu/ml as for *Ralstonia solanacearum*, and low-titer is $10^4$ cfu/ml, mid-titer is $10^5$ cfu/ml, and high-titer is $10^6$ cfu/ml as for *F. oxysporum*.

6. A kit for co-diagnosis of infection of *Ralstonia solanacearum* causing a bacterial wilt disease and *Fusarium oxysporum* causing a fungal wilt disease semi-quantitatively, the kit comprising:
an analysis strip in which a test line having a fixed bed for immunoglobulin G (IgG) antibodies specifically responsive to *Ralstonia solanacearum* and a control line for identifying normal operation are provided in a predetermined area on a membrane,
an analysis strip in which a test line having a fixed bed for immunoglobulin G (IgG) antibodies specifically responsive to *Fusarium oxysporum*, and a control line for identifying normal operation are provided in a predetermined area on a membrane, and
a lower plate on which the said strips are placed and an upper plate covering the lower plate so that the said strips inside are protected from various contaminants,
wherein at least one of a sample inlet for inputting a sample and a result display window for observing a response result in the test line and the control line on the analysis strip is provided in the upper plate.

7. The kit of claim 6, wherein the sample is characterized as plant juice.

\* \* \* \* \*